United States Patent [19]

Wall

[11] Patent Number: 4,651,746
[45] Date of Patent: Mar. 24, 1987

[54] ORAL AIRWAY AND ENDOTRACHIAL MONITOR

[76] Inventor: William H. Wall, 2300 Henderson Mill Rd., Atlanta, Ga. 30345

[21] Appl. No.: 608,183

[22] Filed: May 8, 1984

[51] Int. Cl.$^4$ .............................................. A61B 5/08
[52] U.S. Cl. .................................. 128/670; 128/719; 128/671; 128/716
[58] Field of Search ............... 128/670, 671, 720, 748, 128/768, 787, 630, 638, 642, 716, 725, 734, 760, 719, 724, 784, 780, 207.15, 204.12, 204.23

[56] References Cited

U.S. PATENT DOCUMENTS

| | | | |
|---|---|---|---|
| 3,935,742 | 2/1976 | Rybak | 128/716 |
| 4,069,817 | 1/1978 | Fenole et al. | 128/138 A |
| 4,276,888 | 7/1981 | Smith et al. | 128/719 |
| 4,317,453 | 3/1982 | Heim et al. | 128/719 |
| 4,366,821 | 1/1983 | Wittmaier et al. | 128/719 |
| 4,383,534 | 5/1983 | Peters | 128/671 |
| 4,414,982 | 11/1983 | Durkan | 128/716 |
| 4,417,574 | 11/1983 | Talonn et al. | 128/205.12 |
| 4,417,589 | 11/1983 | Favaloro | 128/716 |
| 4,484,573 | 11/1984 | Yoo | 128/138 A |

Primary Examiner—Edward M. Coven
Attorney, Agent, or Firm—Eric P. Schellin

[57] ABSTRACT

A patient monitor for an airway or endotrachial tube having a liquid detector which alerts an operator to the presence of liquid in a patient's throat. Vital signs sensors are also deployed on the appliance for sensing various body conditions. The fluid detector and the vital signs sensors are electricallly coupled to a microprocessor which operates numeric displays for the vital signs information and visual and audible alarms for the liquid detector and vital signs that are not normal or expected.

9 Claims, 4 Drawing Figures

ORAL AIRWAY AND ENDOTRACHIAL MONITOR

BACKGROUND OF THE INVENTION

1. Field of the Invention

The invention is directed to a patient monitor for monitoring the vital signs of a patient and also detecting the presence of liquid in an oral airway or an endotrachial appliance positioned in a patient's throat.

2. Description of the Prior Art

Respiration devices and alarm systems for such devices, are well known in the art. Alarms are provided for alerting an operator when a patient is not breathing or the patient's breathing is falling outside of a normal breathing pattern. Respiratory devices provided with alarms are disclosed in U.S. Pat. Nos. 3,798,629, 3,802,417, 3,961,627, 4,287,886, 4,366,821, 4,368,740, 4,413,632, and 4,417,589.

In addition to the importance of respiration it is important to monitor other vital functions such as temperature and heart rate to insure patient's body is functioning correctly. A vital signs monitor that monitors heart rate, temperature and environmental oxygen is disclosed in U.S. Pat. No. 4,276,888. It is also known to combine vital signs monitor with a device for monitoring respiration to provide a diagnostic device, see U.S. Pat. No. 3,766,908. Such devices can be made extremely compact with the advancement of microprocessor technology. See U.S. Pat. No. 4,129,125.

Using microprocessors in anesthesia and intensive care to monitor the progress of a patient while also providing alarms signals to an operator to facilitate treatment are very important, see Microprocessors in Anesthesia and Intensive Care, Journal of Medical Engineering and Technology (Vol. 7, No. 6, Nov-Dec 83) by G. J. Ball. The Present invention provides a vital signs monitor that is very compact so that it can be attached to an oral airway or an endotrachial appliance and also detect and alert an operator when liquid needs to be evacuated by the appliance.

SUMMARY

The invention comprises a compact monitor that can be easily mounted on an oral airway or an endotrachial appliance, such as an airway, adjacent to a patient's mouth. A liquid detector is mounted at the bottom of the airway at the deepest location in the patient's throat. The liquid detector is coupled to a microprocessor which monitors the detector and actuates an alarm when liquid is detected.

Sensors for measuring the patient's vital signs are also coupled to the microprocessor. The sensors include a respiration sensor, a pulse sensor and a temperature sensor. All of the sensors are mounted on the airway and produce signals that are transmitted to the microprocessor. The microprocessor processes these signals and formulates a respiration rate, a heart rate and the temperature of the patient.

The microprocessor is coupled to a display means for indicating the vital signs of the patient. The display means comprises numeric indicators that are actuated by the microprocessor to indicate the temperature, heart rate and respiration rate of the patient.

The microprocessor, in addition to generating the proper output for the displays, also compares the sensed vital signs data with expected responses. When a vital sign falls outside of the expected range, an alarm is triggered.

Both the liquid detector alarm and the vital signs alarms first trigger lights which will alert the operator. If the condition persists without being corrected a audible alarm is triggered further alerting the operator.

DETAILED DESCRIPTION

Figure 1:
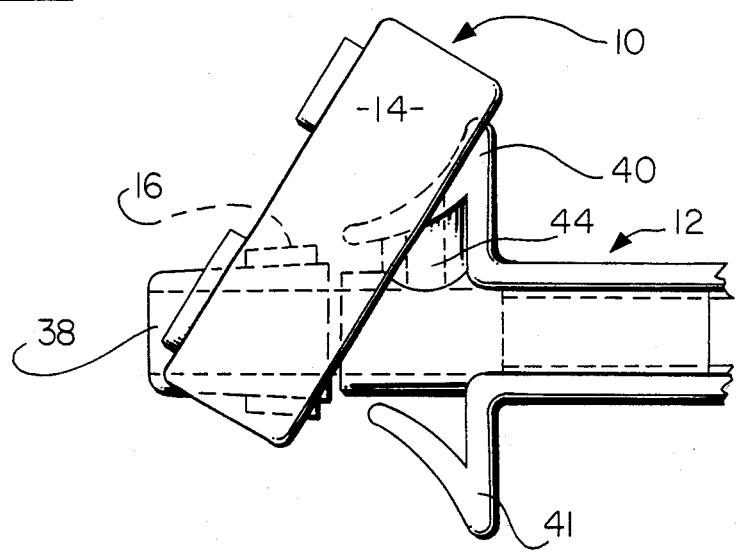
FIG. 1, is a side view of the monitor mounted on an airway.
Figure 2:
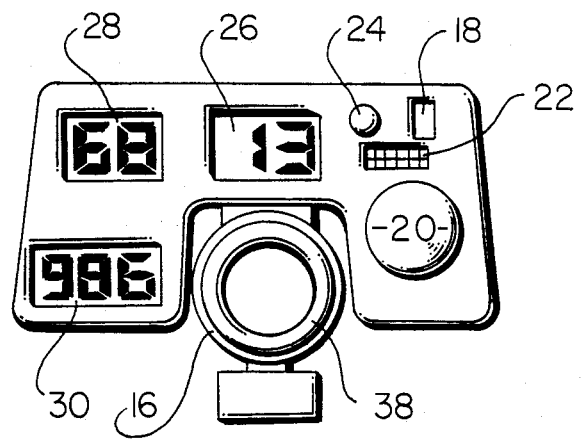
FIG. 2, is a frontal view of the monitor mounted on an airway.

FIGS. 1 and 2 illustrate how the monitor is mounted to airway 12. Monitor 10 comprises a generally rectangular case 14 having mounting tube 16. The front face of case 14, best illustrated in FIG. 2, is provided with on/off switch 18, battery 20, speaker 22, liquid alarm light 24, respiration rate display 26, heart rate display 28 and temperature display 30. Battery 20 is a button-shaped element which can be easily screwed into and out of, the front face of the monitor, similar to batteries used in wrist watches. The displays 26, 28 and 30, are numeric displays which can be formed from conventional liquid crystal displays (LCD), light emitting diodes (LED), or similar display devices.

Figure 3:
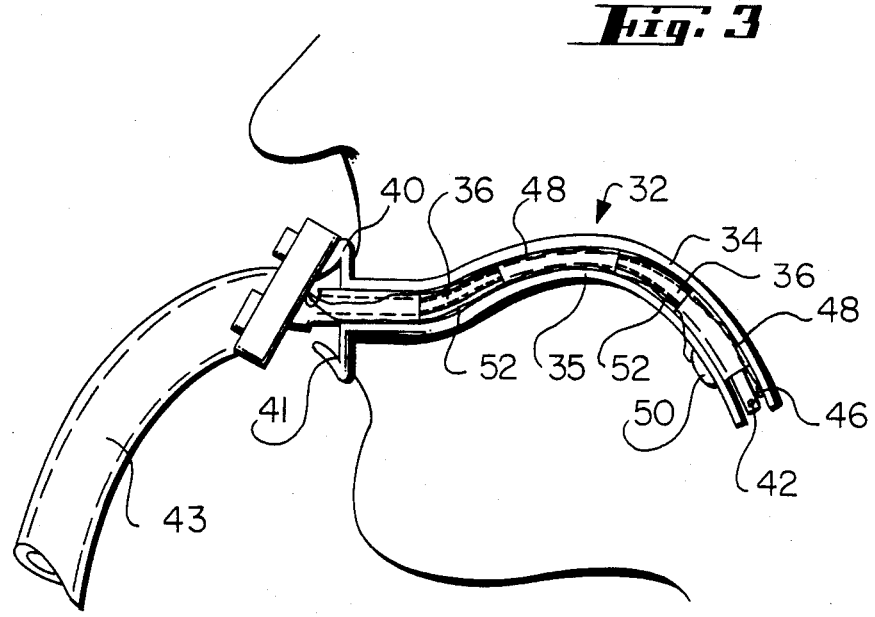
FIG. 3, is a side view of the monitor and airway illustrating the positioning of the sensors in a patient's throat.

For illustration purposes the monitor is mounted on an "Oro-Pharynegeal Suction Airway" disclosed by the inventor in U.S. Pat. Application Ser. No. 577,738, filed Feb. 9, 1984, which is incorporated herein by reference. In broad terms, the airway, best illustrated in FIG. 3, comprises elongated body 32 having parallel flange elements 34 and 35 and tubing 36. The airway is provided with a tapered nipple 38 and lip elements 40 and 41 (see FIG. 1) at one end of the airway adjacent the patient's mouth. The other end of the airway is positioned deep inside the patient's throat and is provided with suction openings 42 which are used to draw liquid from the throat through tubing 14 and out through nipple 38 by means of suction tube 43. Of particular interest is conduit 44 (shown in phantom lines in FIG. 1) which is coupled to the monitor for sensing respiration rate. The above described airway is only discussed for illustration purposes and the subject monitor maybe used in a number applications such as an endotrachial tube or other anathesia applicances that enter the throat of a patient. Therefore the term "airway" will be used throughout as also including endotrachial tubes and other appliances that extend into a patient's throat.

Mounting tube 16 is a conically shaped tube which mates with nipple 38 of the airway. To mount the monitor, tube 16 is aligned with nipple 38 and the monitor and tube are passed down the nipple until the tube is frictionally fitted on the nipple thereby mounting the monitor. The forward portion of nipple 38 is exposed after the monitor has been mounted so that suction tube 43 can also be attached to the nipple.

The monitor is provided with a liquid sensor 46 mounted at the end of the airway which detects the presence of liquid in the throat. Wires 48 electrically couple the liquid sensor to the monitor. Temperature and pulse sensor 50 is mounted to the outside of parallel flange element 35 so that is comes in direct contact with the throat, tongue and lips of the patient. Sensor 50 is electrically coupled to the monitor by wires 52 which run along the airway. Another sensor is built into the monitor and comprises a respiration sensor. Conduit 44 pneumatically couples the monitor with the airway, and as such the change in air pressure caused by the patient's breathing can be sensed and used to generate a respiration rate by the monitor. The specific structure of the sensors is not important, and such sensors are well known in the art. It is only important that the respiration sensor be pneumatically coupled to the respiration passage, that pulse and temperature sensor be in direct contact with the patient and that liquid sensor be positioned as far as possible down into the throat. Although in the illustrated embodiment the pulse and temperature sensors are deployed in a patient's throat these sensors maybe positioned adjacent the mouth contacting a patient's lips.

Figure 4:
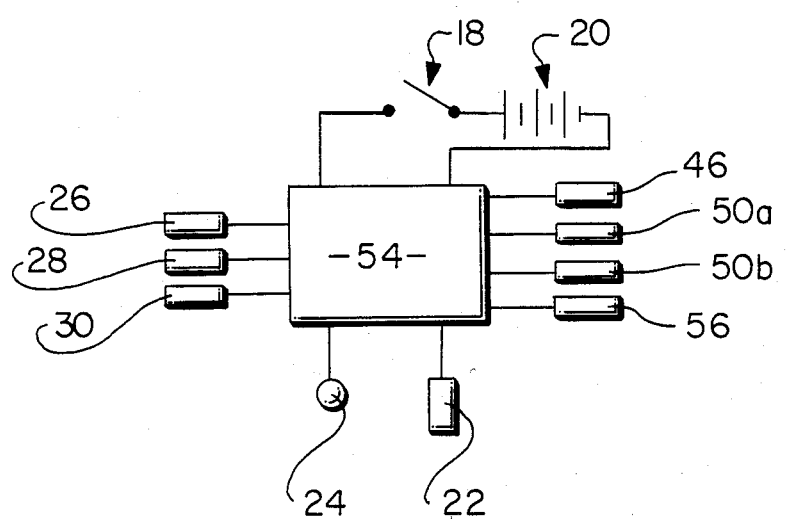
FIG. 4, is an electrical schematic of the monitor.

FIG. 4 illustrates an electrical schematic of the monitor. Microprocessor 54 which comprises the monitor means is powered by battery 20 which is controlled by on/off switch 18. Liquid sensor 46, temperature sensor 50a, pulse sensor 50B and respiration sensor 56 communicate with and are electrically coupled to microprocessor 56. The microprocessor can be any conventional digital microprocessor which is provided with appropriate analog to digital converters for the output signals of the sensors. The microprocessor is also provided with an internal clock which is used in calculating the time dependent respiration and heart rate. However, an external clock providing a timed input could also be used. More specifically the microprocessor on a continuing basis evaluates the output of pulse sensor and the respiration sensor and calculates the appropriate rates. The microprocessor generates respiration rate and heart rate signals that are directed to displays 26 and 28 respectively. The output signal of the temperature sensor is used to provide a temperature output signal that is directed to display 30 for indicating temperature. The liquid sensor also directs a liquid signal to the microprocessor upon detecting liquid in the throat. When liquid is detected the microprocessor actuates alarm light 24.

The microprocessor is also provided with comparison means for comparing the vital signs, that is respiration rate, temperature and heart rate with expected or normal rates. When the detected rate exceeds prescribed limits a visual alarm is activated. The visual alarm may comprise individual lights mounted adjacent to the appropriate displays (not shown) or the appropriate displays themselves maybe be flashed on and off. If the excessive rate persists for longer than a predetermined amount of time, an audible alarm is sounded through speaker 22, to further alert the operator of a serious condition. The liquid alarm circuit functions similarly in that first the visual alarm is activated and then if the presence of liquid persists past a predetermined amount of time the audible alarm is sounded by speaker 22.

In a further refinement of the invention the audible alarm could sound different tones for different alarms. Or possibly a voice synthesizer could be employed to announce the specific problem to the operator.

The invention is not to be limited by the above-description, but is to be limited solely by the claims that follow.

I claim:

1. A patient monitor that is coupled to an airway, said monitor designed for alerting an operator to the presence of liquid in an airway when positioned in a patient's throat; said patient monitor comprising:

liquid detection means which generates a liquid signal upon detection of liquid;

a monitor means, comprising a microprocessor, in electrical communication with the liquid detection means for receiving the liquid signal and generating an electrical liquid alarm signal;

a liquid alarm means in electrical communication with the monitor means for receiving the liquid alarm signal whereby the liquid alarm means is actuated alerting an operator to the presence of liquid;

a respiration sensor, electrically coupled to the microprocessor, for sensing the respiration of a patient generating a respiration signal that is transmitted to the microprocessor, whereby the microprocessor formulates a respiration rate signal; and a respiration rate display means, in electrical communication with the microprocessor for receiving the respiration rate signal and for alerting the operator as to a respiration rate for a patient.

2. A patient monitor as defined by claim 1 further comprising a pulse sensor which is electrically coupled to the microprocessor formulates a heart rate signal that is transmitted to a heart rate display means for alerting an operator as to the heart rate for a patient.

3. A patient monitor as defined by claim 2 further comprising a temperature sensor and a temperature display means, the temperature sensor electrically coupled to the microprocessor and senses the temperature of a patient generating a temperature signal that is transmitted to the microprocessor, the microprocessor transmits the temperature signal to the temperature display means for alerting an operator as to a temperature of a patient.

4. A patient monitor as defined by claim 3 wherein said liquid alarm means comprises a visual means for alerting an operator to the presence of liquid in a patient's throat.

5. A patient monitor as defined by claim 4 wherein the liquid alarm means further comprises an audible alarm means for alerting an operator to the presence of liquid in a patient's throat.

6. A patient monitor as defined by claim 5 wherein the liquid alarm signal comprises a first liquid alarm signal and a second liquid alarm signal, so that when liquid is first detected by the liquid detection means, the monitor means generates a first liquid alarm signal for the visual alarm means, after a specified period of time if liquid is still detected by the liquid detection means the monitor means generates a second liquid alarm signal which actuates the audible alarm means.

7. A patient monitor as defined by claim 6 wherein the respiratory rate display means, the heart rate display means and the temperature display means are numeric displays.

8. A patient monitor as defined by claim 7 wherein the numeric displays are liquid crystal displays.

9. A patient monitor as defined by claim 7 wherein the numeric displays are light emitting diodes.

* * * * *